United States Patent [19]
Kuzma

[11] Patent Number: 6,163,729
[45] Date of Patent: *Dec. 19, 2000

[54] METHOD OF POSITIONING AN IMPLANTABLE COCHLEAR ELECTRODE ARRAY WITHIN A COCHLEA

[75] Inventor: Janusz A. Kuzma, Englewood, Colo.

[73] Assignee: Advanced Bionics Corporation, Sylmar, Calif.

[*] Notice: This patent is subject to a terminal disclaimer.

[21] Appl. No.: 09/429,794

[22] Filed: Oct. 29, 1999

Related U.S. Application Data

[60] Division of application No. 09/216,063, Dec. 18, 1998, Pat. No. 6,078,841, which is a continuation-in-part of application No. 09/140,034, Aug. 26, 1998, Pat. No. 6,038,484.

[51] Int. Cl.[7] ........................................................ A61N 1/05
[52] U.S. Cl. .................................................................. 607/137
[58] Field of Search ........................................ 607/136, 137, 607/55–57; 600/379

[56] References Cited

U.S. PATENT DOCUMENTS 6,038,484  3/2000  Kuzma ..................................... 607/137

Primary Examiner—George R. Evanisko
Attorney, Agent, or Firm—Bryant R. Gold

[57] ABSTRACT

A method of positioning an electrode array within a human cochlea includes making a flexible positioner as a curved or hooked shape from a silicone polymer. The positioner is adapted to be inserted into the scala tympani duct of a human cochlea. The positioner may be inserted into the scala tympani duct before, concurrent with, or after, insertion of the electrode array. The flexible positioner fills space within the scala tympani duct so as to force the electrode array, also inserted into the scala tympani duct, against the modiolar wall of the cochlea, where the electrode contacts of the electrode array may be more effective. In one embodiment, a channeling groove is formed along one side of the positioner for receiving the electrode array. Also, in one embodiment, a silastic tube forms a molded-in tube within the molded positioner, and provides a lumen, sealed or closed at its distal end, into which a stylet wire may be inserted during the insertion process.

19 Claims, 9 Drawing Sheets

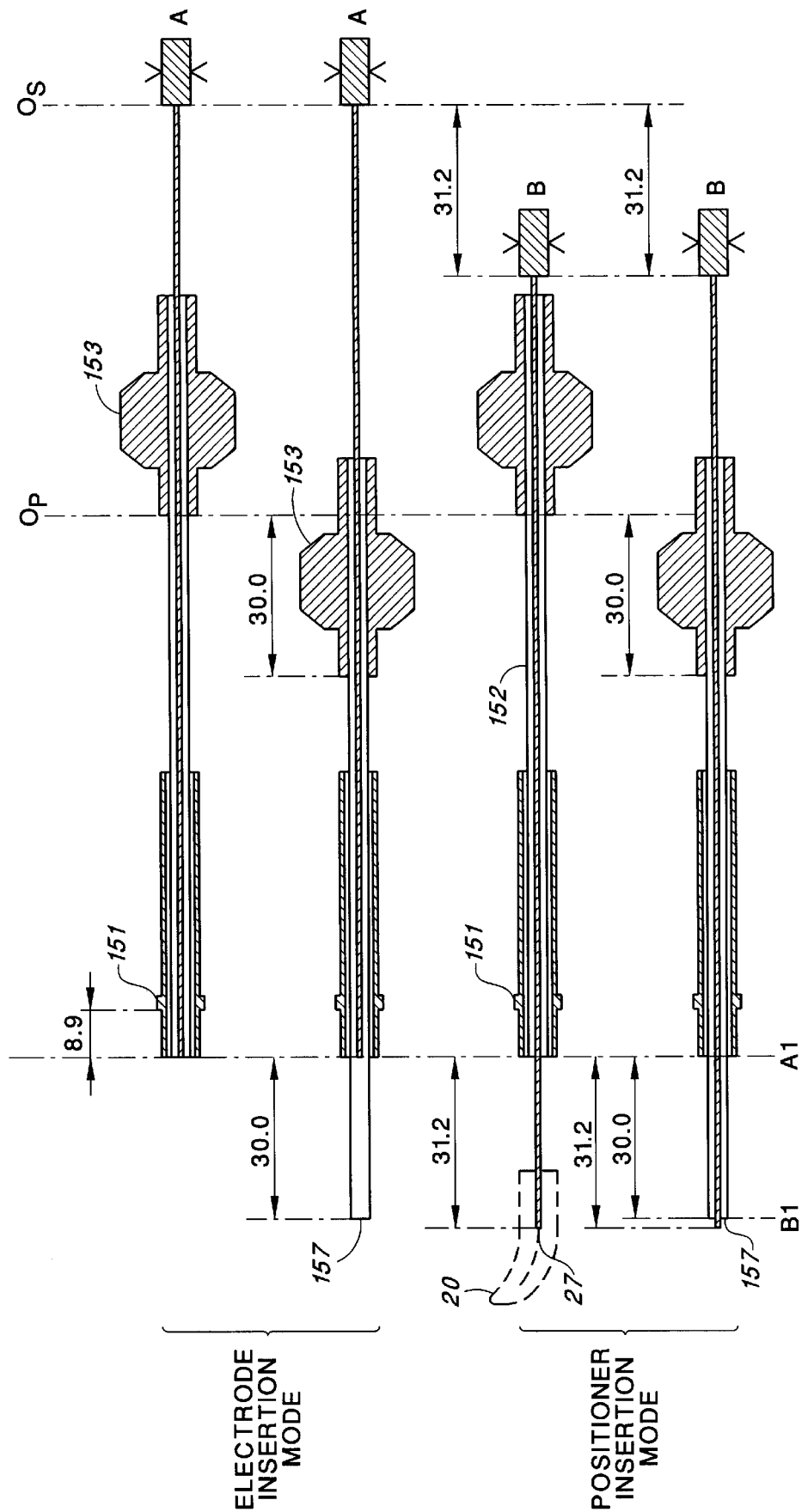

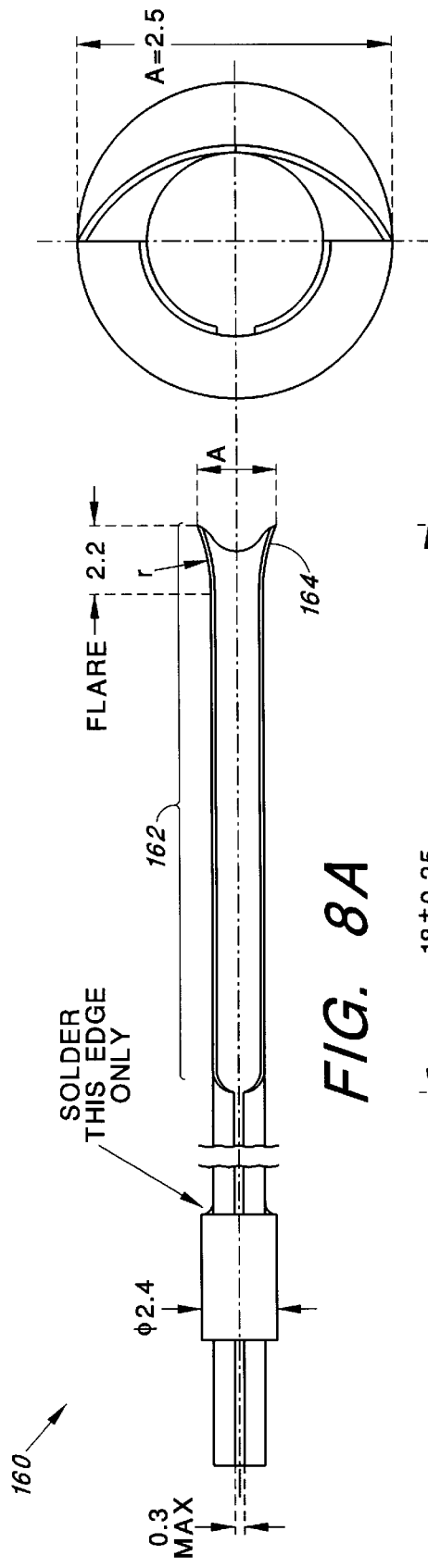
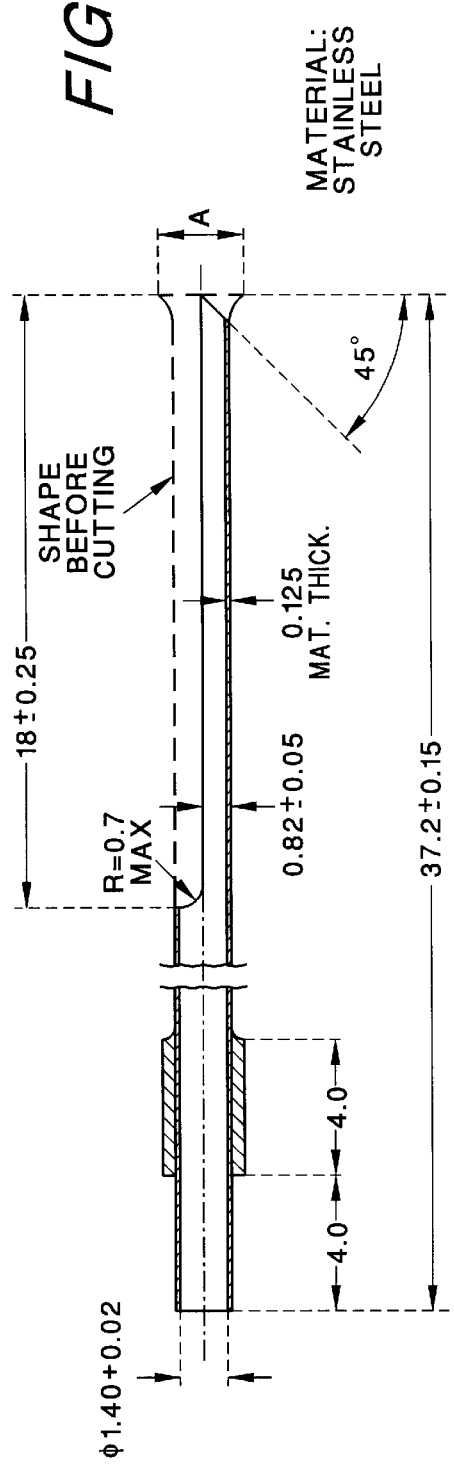
FIG. 8A
FIG. 8B
FIG. 8C

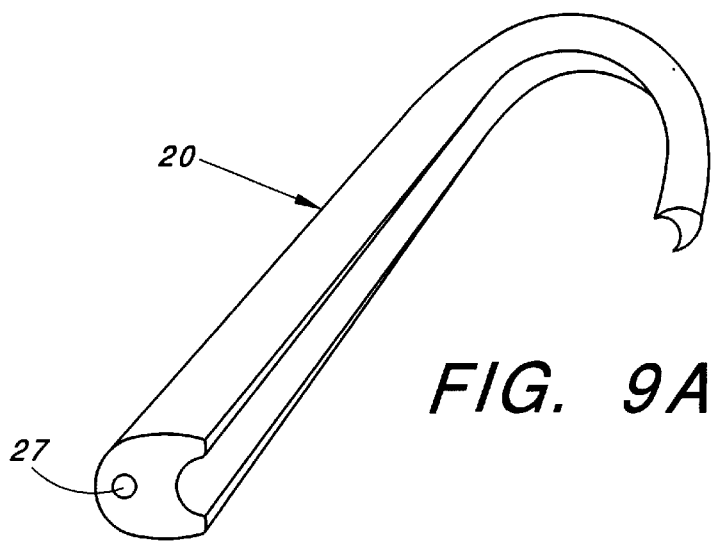
FIG. 9A
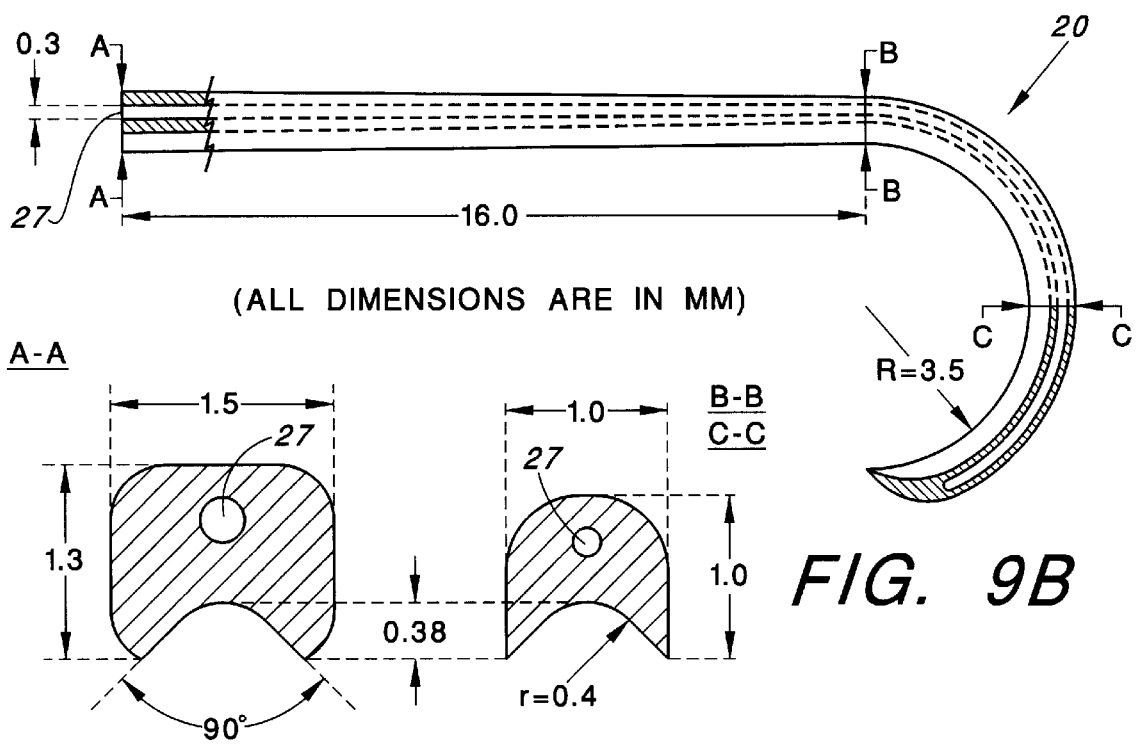
(ALL DIMENSIONS ARE IN MM)
FIG. 9B
FIG. 9C
FIG. 9D

METHOD OF POSITIONING AN IMPLANTABLE COCHLEAR ELECTRODE ARRAY WITHIN A COCHLEA

This application is a divisional of application Ser. No. 09/216,063, filed Dec. 18, 1998, now U.S. Pat. No. 6,078,841 which application is a continuation-in-part (CIP) of application Ser. No. 09/140,034, filed Aug. 26, 1998 now U.S. Pat. No. 6,038,484.

BACKGROUND OF THE INVENTION

The present invention relates to implantable stimulation devices, e.g., cochlear prosthesis used to electrically stimulate the auditory nerve, and more particularly to an electrode array for use with a cochlear stimulator that is designed to hug the modiolus so as to place electrode contacts of the electrode array in close proximity to the ganglion cells and thereby to the auditory nerve fibers.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlear (the hair cells are located in the vicinity of the radially outer wall of the cochlea) by presenting electrical stimulation to the auditory nerve fibers directly, leading to the perception of sound in the brain and an at least partial restoration of hearing function. The common denominator in most of these cochlear prosthesis systems has been the implantation into the cochlea of electrodes which are responsive to suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference. Unfortunately, while the electrode shown in the '647 patent represents a significant advance in the art, there exists lack of sufficient shape memory associated with the electrode to allow it to return to its original curvature (once having been straightened for initial insertion) with sufficient hugging force to allow it to wrap snugly against the modiolus of the cochlea.

It is also known in the art, as shown in applicant's prior patents, U.S. Pat. Nos. 5,545,219 and 5,645,585, to construct an electrode carrier from two initially straight members, a rodlike electrode carrier and a flexible rodlike positioning member. As shown in these patents, the two members extend in substantially parallel relation to and closely alongside each other, but are connected to each other only at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference.

Unfortunately, while the electrode array taught in the above-referenced '219 and '585 patents has the right idea, i.e., to force the electrode carrier into a close hugging engagement with the modiolus, it does so only by use of an additional element that makes manufacture of the lead more difficult and expensive, and only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

Thus, while it has long been assumed that an enhanced performance of a cochlear implant can be achieved by proper placement of the electrode contacts as close as possible to the modiolar wall of the cochlea, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes are generally positioned too far way from the modiolar wall.

It is thus evident that improvements are still needed in cochlear electrodes, particularly to better assure that the electrode assumes a close hugging relationship with the modiolus once implantation of the electrode has occurred.

SUMMARY OF THE INVENTION

The present invention addresses the above and other needs by providing a flexible positioner for use with an implantable cochlear electrode array that allows for positioning of the electrode array against the modiolar wall of the cochlea, thereby placing the electrode contacts of such electrode array as close as possible to the modiolus. The flexible positioner of the invention is typically molded from a silicone polymer so as to make it easy to slide into the cochlea, and is made to assume a curved shape to facilitate its insertion into the cochlea. Advantageously, an insertion tool may be used to facilitate insertion of the positioner into the cochlea, behind the electrode array, so as to force the electrode array to hug the modiolus. Alternatively, the positioner includes a longitudinal channel into which a removable stylet may be inserted in order to help guide the positioner into its desired position within the cochlea.

In accordance with one aspect of the invention, the positioner is easily and inexpensively manufactured by molding implant grade liquid silastic rubber (LSR), or equivalent flexible material, around a length of silastic tubing, held in a curved shape during the molding process, so that the molded positioner naturally assumes a desired curved shape.

Advantageously, the electrode positioner of the present invention may be used with almost any electrode array that is to be inserted into the cochlea in order to assure that a desired modiolar-hugging relationship between the electrode array and the modiolus is achieved.

In use, the electrode array is typically first inserted into the cochlea as far as it reasonably can be in conventional manner. See, e.g., U.S. Pat. No. 5,443,493, incorporated herein by reference. With the electrode array inserted into the cochlea, the positioner is next inserted into the cochlea, behind the electrode array so as to force or push the electrode array against the modiolar wall. A channel or grove along a fronting edge of the positioner receives the electrode array and aids this process of forcing the electrode array against the modiolar wall. Moreover, such channel or grove helps prevent undesirable twisting of the electrode array or positioner as the insertion process takes place. Advantageously, as the positioner is thus inserted into the cochlea behind the electrode array, the positioner may carry the electrode deeper into the cochlea, e.g., approximately ¼ to ½ turn deeper. As needed, or desired, a suitable lubricant may be spread over the surface of the positioner prior to its insertion in order to make its insertion into the cochlea, behind the electrode array, easier.

Alternatively, it is also possible to first insert the positioner into the cochlea, as deep as it reasonably may be inserted, with its groove or channel fronting the modiolus, and then to slide the electrode array into the cochlea, within the groove or channel, thereby causing the electrode array to hug the modiolar wall.

It is an object of the invention to provide a flexible positioner that may be inserted into the scala tympani duct along with a cochlear electrode array that positions the electrode array against the modiolar wall.

BRIEF DESCRIPTION OF THE DRAWINGS

The features and advantages of the present invention will be more apparent from the following more particular description thereof, presented in conjunction with the following drawings, wherein:

FIG. 7B functionally illustrates operation of the tool of the present invention during an electrode insertion mode and during a positioner insertion mode;

FIGS. 8A, 8B and 8C are a top, end, and side view, respectively, of the positioner guiding tube used as part of the insertion tool of the present invention;

FIG. 9A shows a perspective view of a pre-curved positioner that may be used with the invention;

FIG. 9B is a partial side sectional view of the positioner shown in FIG. 9A;

FIG. 9C is a sectional view of the positioner taken along the lines A—A of FIG. 9B;

FIG. 9D is a sectional view of the positioner taken along the lines B—B and/or C—C of FIG. 9B;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The invention described herein teaches the use of a positioner with an electrode array of any type used with a cochlear stimulation system. Different electrodes and electrode systems may be used with the invention, as disclosed, e.g., in Applicant's previously-filed patent application Ser. No. 09/140,034, filed Aug. 26, 1998, incorporated herein by reference. The materials, dimensions, methods of manufacture, and the like, described in this prior-filed patent application, or any of the other previously-referenced patents, are also applicable to the present invention.

Figure 1A:
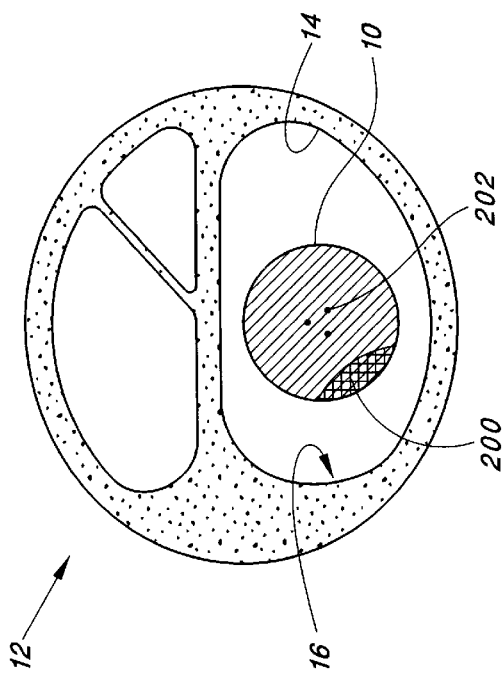
FIG. 1A is a sectional view taken along the line A—A of FIG. 1.
Figure 1:
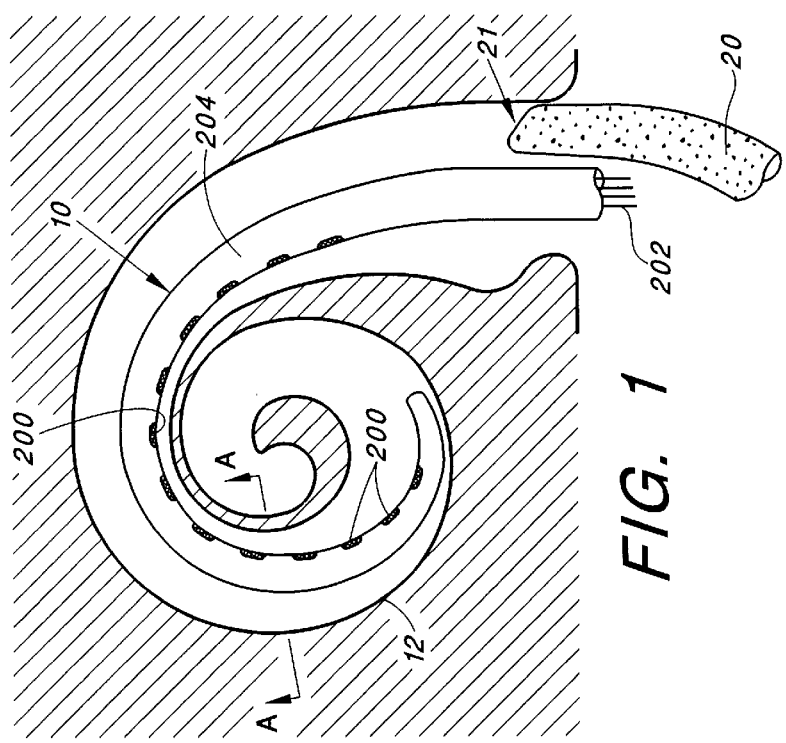
FIG. 1 is a schematic representation of the scala tympani duct of the cochlea showing the electrode array first inserted into the cochlea and showing the positioner inserted second into the cochlea.

As indicated, the positioner of the present invention is adapted to be used with any type of cochlear electrode array, e.g., of the type disclosed in any of the previously-referenced patents or patent application. In general, as illustrated in FIGS. 1 and 1A (which shows a typical electrode array 10 inserted into the scala tympani duct 14 of a cochlea 12), an electrode array 10 includes a plurality of spaced-apart electrodes 200, formed within a flexible carrier 204. Each of the electrodes is connected to at least one wire 202 which is embedded within the carrier 204. A proximal end of the these wires 202 (not shown) allows selective electrical connection to be made with each electrode 200 through use of a tissue stimulator, e.g., a cochlear stimulator. The tissue stimulator, in turn, causes an electrical stimulus to appear between a selected pair of the electrodes 200, which stimulus is designed to provide direct electrical stimulation of the auditory nerve cells.

Also shown in FIG. 1 is the distal tip 21 of a flexible positioner 20 made in accordance with the invention as the positioner is just starting to be inserted into the scala tympani duct 14 behind the electrode array 10. As will become more evident from the description that follows, the flexible positioner 20 is preferably made from a silicone polymer, and is molded to assume a generally curved shape, with a width or cross-sectional area that is tapered, as required, to match the cross-sectional area or width of the scala tympani duct within the cochlea. The radius of curvature "R" is selected to be somewhat larger than the natural curvature of the scala tympani duct. That is, when inserted into the scala tympani, the positioner 20 will have to assume a tighter wind or coil than that afforded by its formed curved shape. This assures that when inserted into the cochlea, the positioner 20 is held away from the modiolus wall 16, leaving a cavity or channel against the modiolus wall wherein the electrode array may be placed or positioned. Further, this preferred shape and positioning of the positioner within the cochlea improve the directional stability of the electrode array during insertion, i.e., help prevent rotation of the electrode array, thereby assuring that the electrode array 10 remains positioned adjacent the modiolus wall 16.

A preferred technique for inserting the electrode array 10 into the cochlea 12 is to first insert the electrode array 10 into the scala tympani 14 using any suitable technique, as is known in the art. If possible, during such insertion, the electrode contacts 200 of the electrode array 10 should be oriented to face the modiolar wall 16 within the cochlea. Whether this is possible or not depends on the type of electrode array which is used. An electrode array of the type disclosed in Applicant's copending patent application, Ser. No. 09/140,034, previously referenced, is specifically designed so that all of the electrode contacts may face the same direction. Such electrode array can be oriented so that all of the electrode contacts 200 face the modiolar wall, which is a preferred orientation. Other electrode arrays, however, have electrode contacts that are offset so as not to face in the same direction, or have annular ring electrodes. In such instance, the electrode array is simply inserted into the scala tympani in conventional manner.

Regardless of the type of electrode array 10, when the electrode array is first inserted into the scala tympani 14, it typically tends to move towards the outer wall of the scala tympani, farthest away from the modiolar wall 16. That is, as seen in the schematic representation of FIG. 1, as well as the sectional view of FIG. 1A, when first inserted into the cochlea, the electrode array 10, including its electrode contacts 200, are not firmly held in position against the inner wall (modiolus) 16 of the cochlea. In order to force or hold the electrode array 10 up against the modiolus, the positioner 20 is also inserted into the cochlea, behind the electrode array 10, i.e., on the side of the electrode array 10 farthest from the modiolus, as seen in FIG. 1 (which shows the distal tip 21 of the positioner 20 just as it is first inserted behind the electrode array 10 within the cochlea).

As the positioner 20 is pushed deeper into the cochlea, it forces the electrode array 10 up against the modiolar wall 16, which action causes many of the electrode contacts 200 to be in direct contact (touching) with the modiolar wall. Moreover, as the positioner 20 is pushed still deeper into the cochlea, the movement of the positioner against the electrode array may tend to carry the electrode array 10 even deeper into the cochlea, e.g., causing the electrode array 10 to be inserted an additional ¼ to ½ turn deeper into the cochlea than when initially inserted.

Figure 2:
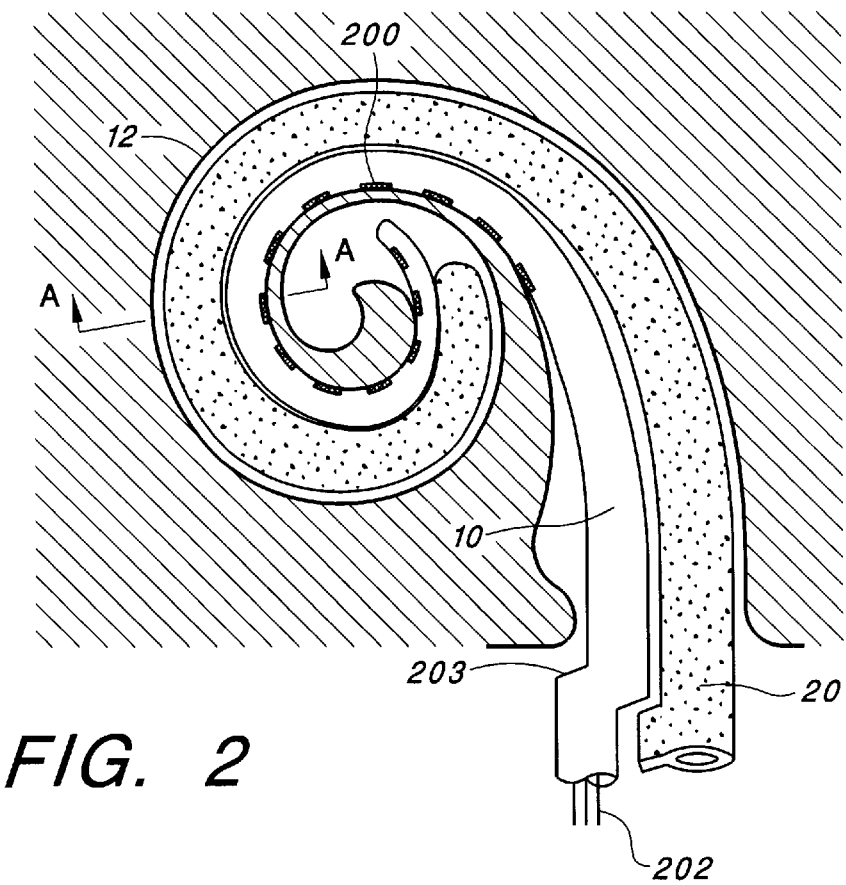
FIG. 2 is a schematic representation of the scala tympani duct of the cochlea as in FIG. 1, but showing the positioner fully inserted into the cochlea.
Figure 2A:
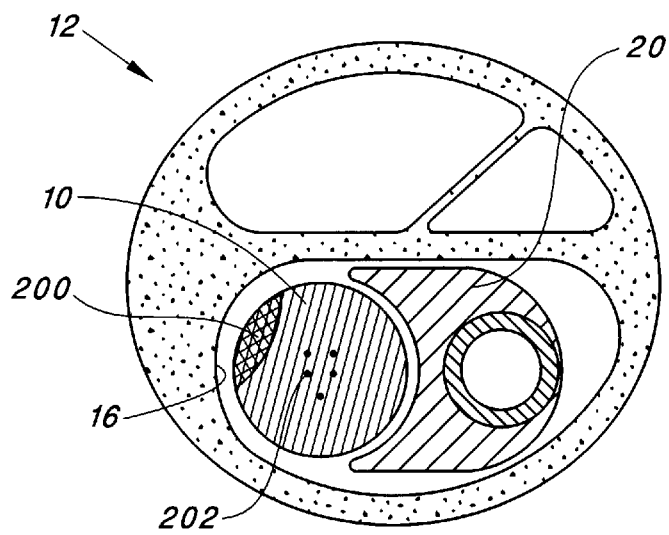
FIG. 2A is a sectional view of the cochlea taken along the line A—A of FIG.2.

A fully inserted electrode array 10 with positioner 20 is shown in FIGS. 2 and 2A. Note that the positioner 20 fills the available space within the scala tympani 14 and pushes the electrode array 10 up against the modiolar wall 16, as desired. A groove or channel 22 is formed along one side or edge of the positioner 20 to receive the electrode array 10 as the positioner is inserted into the scala tympani duct.

To aid in the insertion process, a suitable lubricant may be spread over the surface of the positioner 20, e.g., to form a coating thereon, prior to inserting it into the scala tympani duct behind the electrode array 10. Any suitable lubricant, e.g., a silicone oil lubricant, may be used for this purpose. Such lubricants, or equivalent lubricants, have been used for years in order to help implant pacemaker leads. The use of equivalent lubricants, or other surface preparation techniques, is described, e.g., in United States Pat. No. 5,736,251, incorporated herein by reference.

As seen best in FIG. 2, it should be noted that typically the electrode array 10 has an offset 203 associated therewith. Such offset 203 functions as a stop to prevent the electrode array 10 from being inserted too deep into the cochlea. Even when such offset cannot effectively function as a stop, it can always function as a mark, to aid the physician to know when the desired insertion depth has been achieved.

A preferred embodiment of the positioner 20 is illustrated in FIGS. 3, 3A, 3B, and 4. As seen best in FIG. 3, the positioner 20 assumes a general shallow hook shape. (Note, "shallow", in this context, refers to the fact that a distal tip or end portion 21 of the positioner bends only slightly more than 90 degrees, e.g., 120 degrees, from the longitudinal axis or center line of the positioner at the proximal end.) While a shallow hook shape is preferred for purposes of the positioner, it is to be emphasized that any curve shape may suffice, and indeed, no curve shape may also suffice when the body of the positioner is sufficiently flexible so that it can readily bend and conform to the contours of the spiral-shaped scala tympani.

The positioner 20 preferably includes a channel or lumen 27 that passes longitudinally through the entire length of the body of the positioner. Typically, such channel 27 comprises the lumen of a silastic tube 23, which tube 23 forms the core of the positioner. That is, as explained in more detail below, during manufacture of the positioner 10, the silastic tube 23 has liquid silastic material molded and cured around it in order to form the positioner in the desired shape. In this manner, the silastic tube 23 becomes a tube molded into the positioner, or a "molded-in tube". At the distal tip 21, as seen best in FIG. 3, a plug is placed to block the distal end of the channel 27. Such channel or lumen 27 may be used to receive a guiding wire stylet, as also explained below.

Figures 3, 3A, 3B, 4:
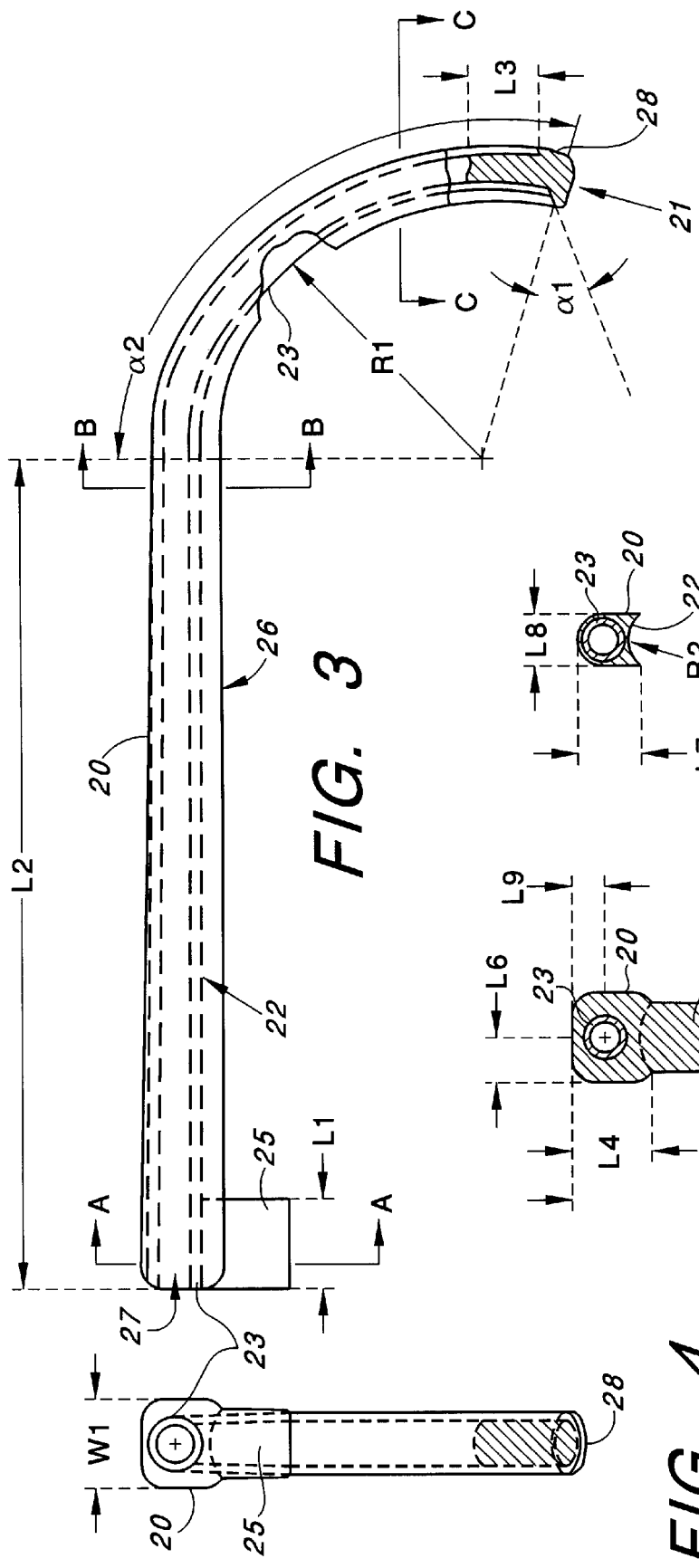
FIG. 3 illustrates a side profile view of a positioner made in accordance with the invention, and further illustrates a desired curve of the positioner at its distal tip.
FIG. 3A is a sectional view taken along the lines A—A of the positioner of FIG. 3.
FIG. 3B is a sectional view taken along the line B—B or C—C of the positioner of FIG. 3.
FIG. 4 is a proximal end view of the positioner of FIG. 3.

A side channel or groove 22 is formed along one edge or side of the positioner body along its entire length, i.e., along the bottom side 26 (or inside-curve side) as the positioner is oriented in FIG. 3. Moreover, the positioner 20 is preferably tapered, as illustrated generally in the sectional views of FIGS. 3A, and 3B, which views are taken respectively at the lines A—A (FIG. 3A), and B—B or C—C (FIG. 3B) of FIG. 3. The cross-sectional area of the positioner at the section lines A—A is roughly W1×L4, whereas the cross-sectional area of the positioner at the section lines B—B or C—C is roughly L7×L8, where W1, L4, L7 and L8 are representative dimensions, having typical values as indicated below.

A guiding tab 25 is also formed at the proximal end of the positioner 20 on the bottom side 26 (the same side as the groove or channel 22). Such tab 25 is used to help keep the positioner properly oriented without twisting as it is inserted into the cochlea, as explained in more detail below in conjunction with the description of FIG. 7, which figure shows a schematic representation of a preferred insertion tool.

Typical dimensions of a cochlear positioner made in accordance with this preferred embodiment of the invention are as identified in FIGS. 3, 3A, 3B and 4 and as presented below. Such dimensions and shape are not intended to be limiting, but are presented merely to show a preferred and best mode for the positioner. Other dimensions and shapes could, of course, be used so long as the positioner is able to fulfill its basic function of forcing or pushing the electrode array against the modiolar wall of the scala tympani duct. Further, a molded-in tube may or may not be used as a core element of the positioner. All dimensions and shape are allowed to change due to relaxation of the molded-in tube.

Referring, then, to the preferred embodiment of the positioner shown in FIGS. 3, 3A, 3B and 4, the length L1 of the tab 25 is typically 0.069±0.008 inches. The length L2 of the straight portion of the positioner is about 0.61 inches. The depth L3 that the plug 28 is inserted into the distal tip of the channel 27 is about 0.04 inches. The height L4 of the positioner at is proximal end, from the edge of the tab 25 to the top side of the positioner, is about 0.051 inches. The length L5 from the top side of the positioner, at its proximal end, to the bottom edge of the tab 25 is about 0.091 inches.

The width W1 of the positioner at its proximal end is about 0.059 or 0.060 inches, making the distance L6 from the center of the tube 23 to the side of the positioner, at its distal end, about 0.03 inches. The distance L9 from the center of the molded-in tube 23 to the top of the positioner, at its distal end, is about 0.012–0.013 inches. The width W2 of the tab 25 is approximately 0.039 inches.

The overall dimensions (cross-sectional shape) of the positioner linearly taper from its proximal end to approximately the end of the straight section L2, e.g., at about the point where the cross-sectional line B—B is placed. At the section line B—B, the dimensions are as shown in FIG. 3B, with the height L7 and the width L8 of the positioner being about 0.037 and 0.039 inches respectively.

The molded-in silastic tube 23 has an inner diameter (I.D.) of about 0.012 inches and an outer diameter (O.D.) of 0.025 inches, making the thickness of the tube walls about 0.006–0.007 inches. The bottom of the grove or channel 22 is formed so as to be near the edge of the tube 23 at the proximal end of the positioner and at the edge of the tube 23 at the distal end of the positioner. The radius R2 associated with the formation of the curved channeling groove 22 is typically about 0.016 inches. This radius R2 remains more or less the same along the entire length of the positioner.

The shallow hook at the distal end of the positioner is formed to have a radius of curvature R1 of about 0.117 to 0.197 inches. The curved or hooked distal tip 21 of the positioner curves at the radius R1 for an angle $\alpha 2$ of about 120 degrees beginning from the point where the straight section L2 ends and the curved or hooked section begins. Further, the distal tip 21 of the molded-in tube 23 is cut at an angle $\alpha 1$, where $\alpha 1$ is defined as shown in FIG. 3, before placement of the plug 28. In the preferred embodiment, the angle $\alpha 1$ is approximately 45 degrees.

Figure 5A:
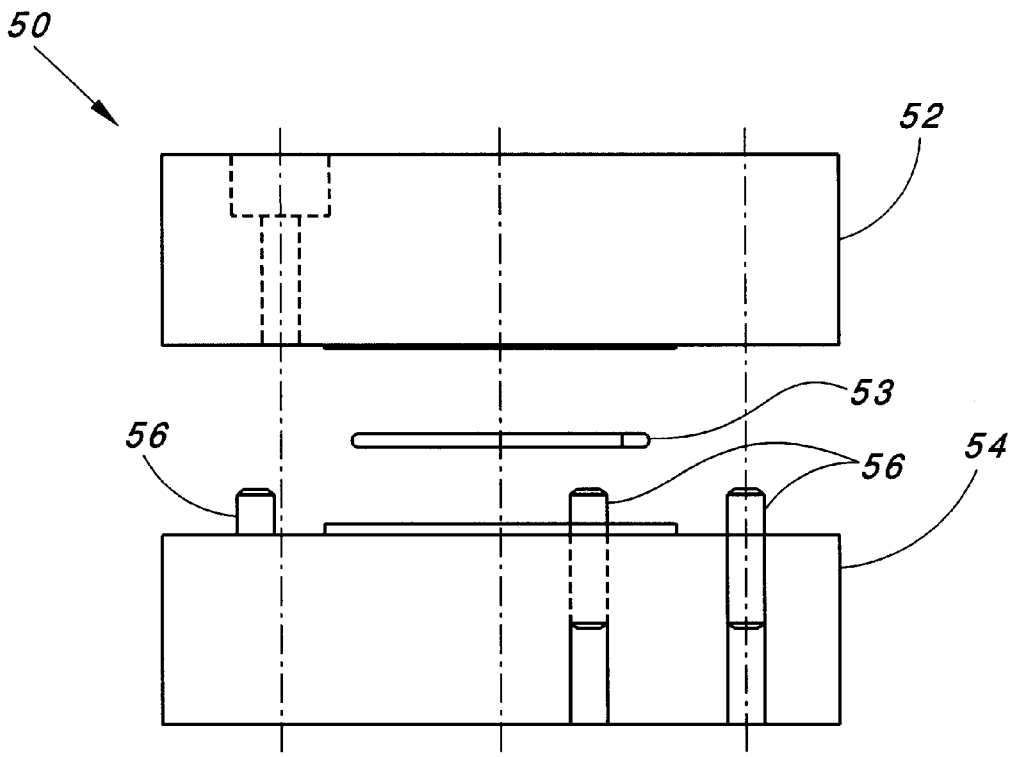
FIG. 5A illustrates a side view of a two-part mold that may be used to make the positioner of FIG. 3.

The positioner 20 is made using a mold 50, illustrated in FIG. 5A. Conventional molding techniques and principles are used to form the positioner 20, as are known to those of skill in the molding art. As seen in FIG. 5A, the mold has a top plate 52 and a bottom plate 54. As seen in both FIGS. 5A and 5B, the mold 50 basically includes removable stainless steel alignment pins 56 at key locations that align the top plate 52 with the bottom plate 54 when the two plates are attached together. Additionally, threaded holes 58 are provided to allow bolts or screws (not shown) to detachably secure and clamp the top plate 52 to the bottom plate 54 during the molding operation.

Figure 5B:
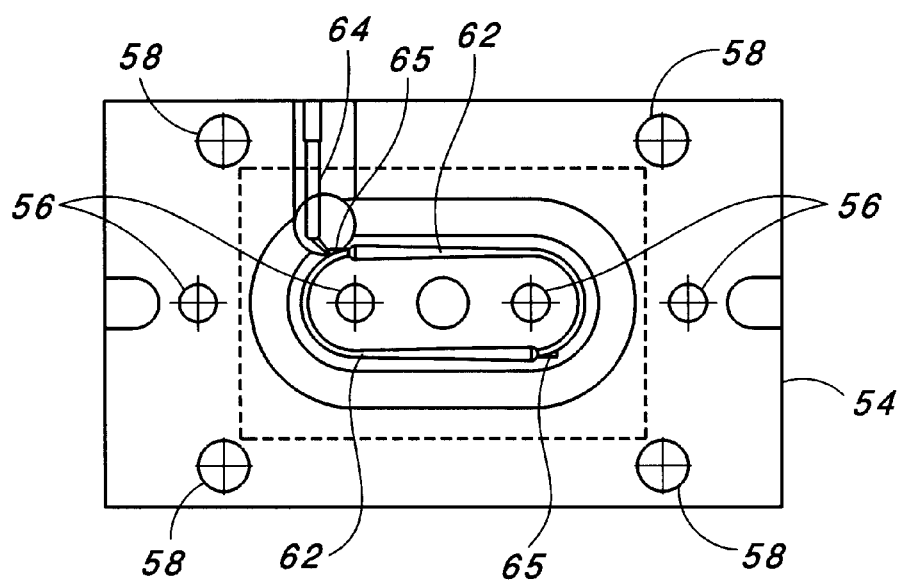
FIG. 5B illustrates a top view of the bottom part of the mold depicted in FIG. 5A.

Half channels 62 are formed in the top plate and bottom plate that define the desired shape of two positioners placed distal-tip-to-proximal-end. Only the bottom plate is shown in FIG. 5B, but the top plate has similar channels formed therein that are the mirror image of those shown in FIG. 5B. That is, two positioners 20 are molded simultaneously using the mold 50. The distal tip of each molded positioner is extended around its radius of curvature approximately another 60° in the mold. The desired shape of the positioner is as shown in FIGS. 3, 3A, 3B and 4. The excess distal tip portion, i.e, the extra 60° or so of curvature, is removed by trimming the distal tip after the positioner(s) has been formed and removed from the mold, as explained below. An injection port 64, which is in fluid communication with the half channels 62, is provided within the top and bottom plates to allow a liquid silastic mixture to be injected into the mold. A stop 65 provides a location for holding one end of a formed wire, placed inside of the proximal end of the lumen of the silastic tube during the molding operation, as also explained below. A mold insert 53, similar to an O-ring, is further placed between the top plate 52 and the bottom plate 54, surrounding the half channels 62, during the molding process.

Figure 6:
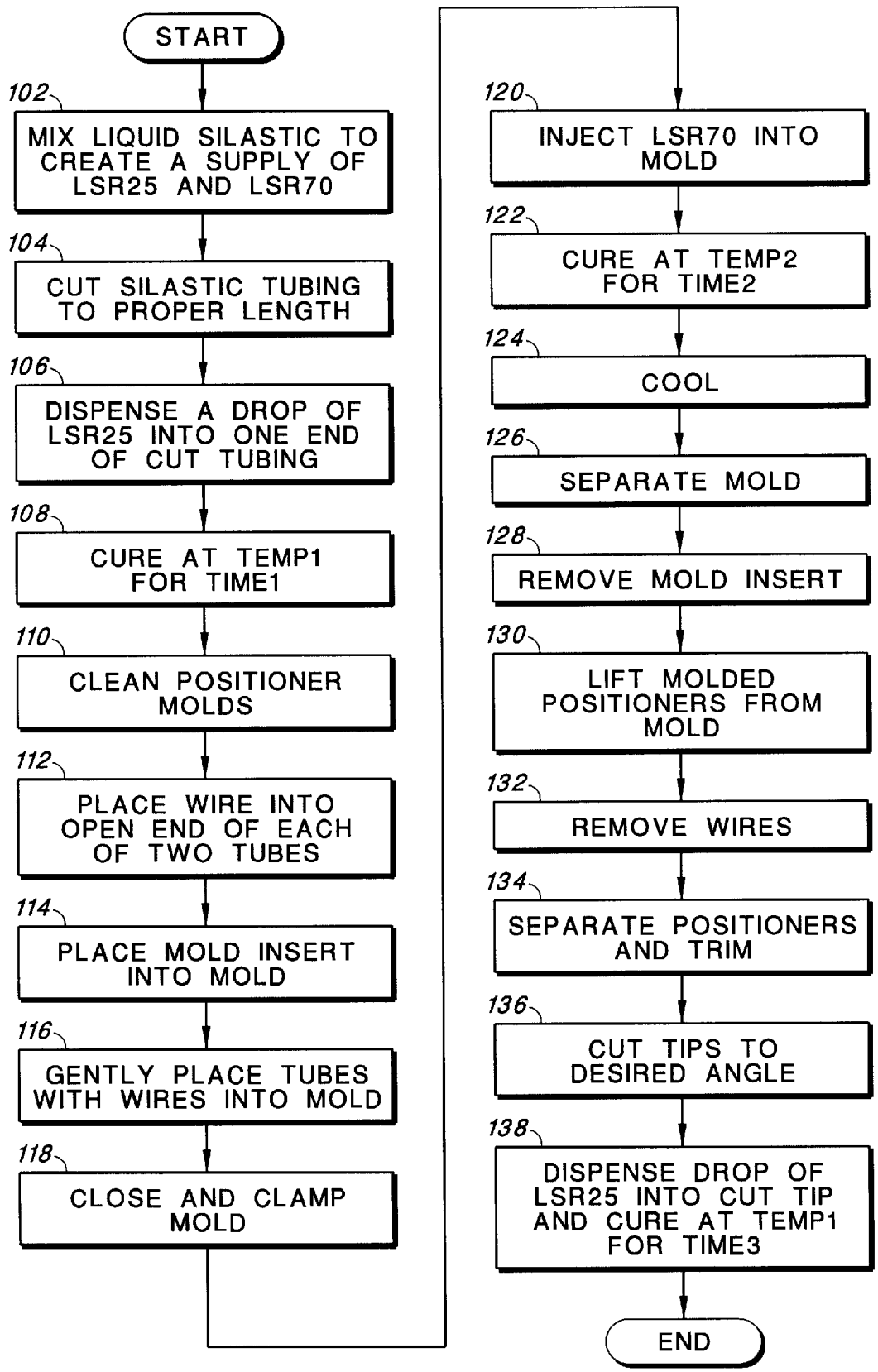
FIG. 6 shows a flow chart of a preferred manner of making the positioner of FIG. 3.

Turning next to FIG. 6, a simplified flow chart of the preferred manner of making a positioner 20 in accordance with the present invention is depicted. As illustrated in FIG. 6, a first step (block 102) relates to mixing implant grade liquid silastic rubber (LSR) to create a supply of LSR25 and a supply of LSR70. The number associated with the "LSR" relates to the properties and cure time of the LSR. Thus, for example, LSR25 cures faster than does LSR70 if allowed to cure at the same temperature. Implant grade liquid silicone rubber (LSR) may be obtained commercially from numerous sources, e.g., Applied Silicone Corporation, 320 W Stanley Avenue, Ventura Calif., 93001. Like epoxy, two portions of the LSR must be mixed together before the curing process begins. Preferably, the mixtures of LSR25 and LSR70 are appropriately degassed in a vacuum chamber for approximately ten minutes. Degassing may also occur by loading the LSR mixtures into syringes, and then centrifuging. Once degassed, the respective mixtures are labeled and placed in appropriate containers, e.g., respective syringes.

Next, commercially available silastic tubing is cut to the proper length (block 104). As indicated previously, the silastic tubing used as the molded-in tube has an I.D. of about 0.012 inches and an O.D. of 0.025 inches. A drop of LSR25 is then dispensed into one end of the cut tubing (block 106). The cut lengths of tubing, with LSR25 dispensed into one end, are then cured in an oven at a temperature TEMP1 of 100° C. for a time period TIME1 of ten to fifteen minutes (block 108).

The positioner mold 50 is then cleaned (block 110) using alcohol or Heptane and lint-free applicators to remove any debris or silastic from a previous use. After cleaning, the molds are dried using compressed air. Next, a length of wire having an O.D. that allows it to be snugly and removably inserted into the channel or lumen 27 of the silastic tube (also referred to as a silicone tube) is inserted into the open end of each tube (block 112). Typically, this length of wire is 17 mm, and it is inserted about 14 mm, leaving about 3 mm of the wire protruding form the open end of the tube. A preferred wire for this purpose is a length of Nitinol wire, marked appropriately so as to identify the 3 mm that need to remain protruding from the tube. The wire thus inserted temporarily seals the proximal end of the tube, and helps position the tube within the mold.

Next, the mold insert 53 is inserted into the bottom plate 54 of the mold (block 114). Then, the tube with the wire inserted therein is placed into the mold, with the protruding end of the wire (the proximal end of the tube) being secured against the end stop 65 of the mold. As required, the tube is gently pressed into its channel, using tweezers or a probe, to assure that all mold cavities are filled.

The mold 50 is then closed and clamped shut (block 118), using the bolts or screws that are threadably inserted into the threaded holes 58. About 0.155 cc of LSR70 is then injected into the mold through the injection port 64 (block 120). Some silastic may emerge from a vent hole of the mold during this injection process. The mold is next placed into a hot press and cured at a temperature TEMP2 of about 300° C. for a time period TIME2 of about five minutes (block 122). The mold is then removed from the hot press and allowed to cool (block 124). When cool enough to comfortably handle, the bolts or screws are removed and the mold halves are separated (block 126). A suitable tool, such as a #1 slotted screwdriver, may be used to help pry open the mold, as required.

Once the mold halves are separated, the mold insert 53 is carefully removed (block 128). Next, the positioners are removed from the mold (block 130). If necessary, the alignment pins 56 may be removed for ease of working with the mold. The wires are removed from each positioner (block 132) and the positioners are separated using, e.g., side cutters (block 134). Each positioner is then placed on a mandrel and the tips are cut at the desired angle $\alpha 1$ (block 136). Any flashing may be trimmed off using the side cutters or micro-scissors.

Once cut and trimmed, the positioners are then preferably cleaned by placing them into a beaker of alcohol and placing the beaker into an ultrasonic cleaner, filled about half way with water. After cleaning and drying, a drop of LSR25 is dispensed into the distal tip 21 in order to form the plug 28. With the drop of LSR25 in place, the positioner is again cured at temperature TEMP1 (about 100° C.) for a time period TIME3 of about 2 hours (block 138). After being thus formed, the positioners are inspected to verify that they are sealed on the 45° angle end, to verify that they are free of flash over 0.005 inches, and finally to verify that they are free of residue and contamination.

Figure 7A:
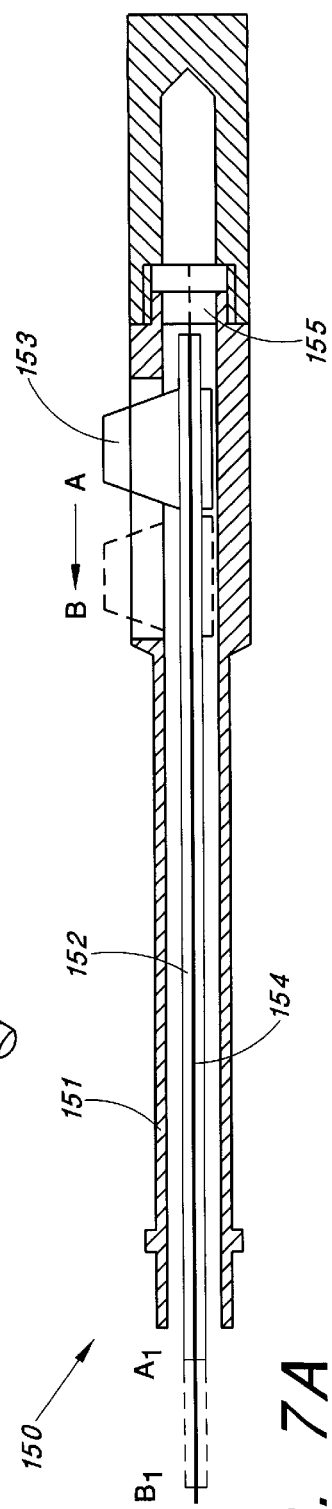
FIG. 7A is a side sectional view of an insertion tool made in accordance with the invention.

Turning next to FIG. 7A, there is shown a side sectional view of an insertion tool 150 that may be used to insert a positioner 20 made in accordance with the invention. The insertion tool 150 has a distal end and a proximal end. The tool 150 includes a main body 151 which houses a slidable pushing tube 152 to which a knob (or handle) 153 is attached at the proximal end. A stylet 154 resides inside the tube 152. A base 155 of the stylet provides a means for pushing the stylet from a retracted position (shown in FIG. 7A) to an extended position (not shown in FIG. 7A).

Note in FIG. 7A that the knob or handle 153 attached to the pushing tube 152 may traverse a distance within the main body from position "A" (shown in FIG. 7A) to position "B" (shown in FIG. 7A by the dashed or phantom lines). Such movement causes the distal end of the pushing tube 152 to move from position "A1" (shown in FIG. 7A) to position "B1" (shown by dashed lines in FIG. 7A). As will be evident from the description which follows, it is the distal end 157 of the pushing tube 152 which contacts the positioner 20, when such is held in place by the distal end of the stylet 154, and pushes it deeper into the cochlea during an insertion operation.

As also evident in FIG. 7A, the base 155, or proximal end of the stylet 154 may also slide within main body 151 from its retracted position (shown in FIG. 7A) to an extended position (not shown in FIG. 7A), wherein the base 155 moves to the left (as oriented in FIG. 7A) until it is up against the knob 153 of the pushing tube 152 when at position "B".

The pushing tube 152 may advantageously be made from a flexible material, e.g., silicone rubber, so that, as required, it may also bend as it pushes the electrode array or positioner deep into the cochlea. In contrast, the main body 151, and in particular positioner guiding tube 160 (which forms a substantial part of the main body, and which is described in more detail below in FIGS. 8A, 8B and 8C), is typically made from a stiff material, e.g., stainless steel.

A key to use of the insertion tool 150 is to include a guiding channel, duct or lumen 27 that passes longitudinally through the item being inserted, e.g., through the positioner 20, into which the distal tip of the stylet 154 may be placed.

Turning next to FIG. 7B, operation of the tool 150 is illustrated. During an electrode insertion mode (top two illustrations in FIG. 7B), the insertion tool is placed in one of two positions. In a first position (top diagram in FIG. 7B), the stylet 154 remains locked in a fully retracted mode, and the pushing tube 152 is also pulled back to a fully retracted position (position "A" in FIG. 7A). While in this position, the electrode array is placed within the main body so that the distal end of the stylet passes through a hole 27' of the electrode array. Then, the handle or knob 153 is pushed towards the distal end of the tool. This action causes the pushing tube 152 to assume an extended position, as shown in the second to the top diagram of FIG. 7B. During this process, the distal end 157 of the pushing tube 152 engages the electrode array and causes it to be inserted deeper into the cochlea. This action may be repeated, as necessary, until the electrode array has assumed its desired insertion depth, or a depth that is close to the desired insertion depth. (Insertion of the positioner behind the electrode array will typically also move the electrode array somewhat deeper into the cochlea.)

The bottom two diagrams in FIG. 7B illustrate a positioner insertion mode of the tool 150. For this mode, the stylet is moved so that its distal tip ends out past the distal end of the main body, or housing, 151; and the pushing tube 152 is retracted back to its "A" position (see FIG. 7A). With the distal tip of the stylet thus extended, and the pushing tube retracted, the positioner 20 may be easily threaded on the stylet 154 by inserting the distal tip of the stylet into the guiding hole or lumen 27 that passes longitudinally through the positioner 20. Once the positioner 20 has been thus threaded onto the distal end of the stylet, the pushing tube is moved to its extended position, as shown in the bottom diagram of FIG. 7B. This causes the distal end 157 of the pushing tube 152 to engage the positioner 20 and push it deeper into the cochlea.

Advantageously, the maximum slide distances of the stylet 154 and the pushing tube 152 may be selected to provide the proper insertion depth into the cochlea. Preferred dimensions and travel distances are evident from the dimensions shown in the drawings, e.g., shown in FIG. 7B.

Next, with reference to FIGS. 8A, 8B and 8C, there is shown top, end, and side views, respectively, of the positioner guiding tube 160 that forms a main component of the main body 151 of the insertion tool 150. As seen in these figures, such positioner guiding tube 160 includes a distal barrel portion 162 that is cut away to provide a half cylinder, with a somewhat flared distal tip 164. The distal end of the pushing tube 152 rests within the channel formed by the half cylinder barrel portion 162.

A proximal portion of the main body 151 (not shown in FIGS. 8A, 8B and 8C) provides the means for allowing the handle or knob 153 of the pushing tube 152, as well as the base portion 155 of the stylet 154, to assume one of two extreme positions, as shown in FIG. 7A and FIG. 7B.

FIG. 9A shows a perspective view of one type of a pre-curved positioner 20 that may be used with the invention. FIGS. 9B, 9C and 9D show various sectional views of the positioner. Such positioner 20 may be as described previously in connection with FIGS. 3, 3A, 3B and 4, or as disclosed in the referenced patent applications. However, an important element of the positioner 20 is the hole, duct, lumen or channel 27 that passes longitudinally through almost the entire length of the positioner. It is through this hole or channel 27 that the distal tip of the stylet 154 is placed during the insertion process. When the positioner 20 is threaded onto the distal end of the stylet 155, then the distal edge of the pushing tube 152 is able to push the positioner deeper into the cochlea while maintaining contact with the positioner. That is, the positioner cannot slip away from the distal tip 157 of the pushing tube 152 when the positioner 20 is threaded on the stylet 154.

Figure 10:
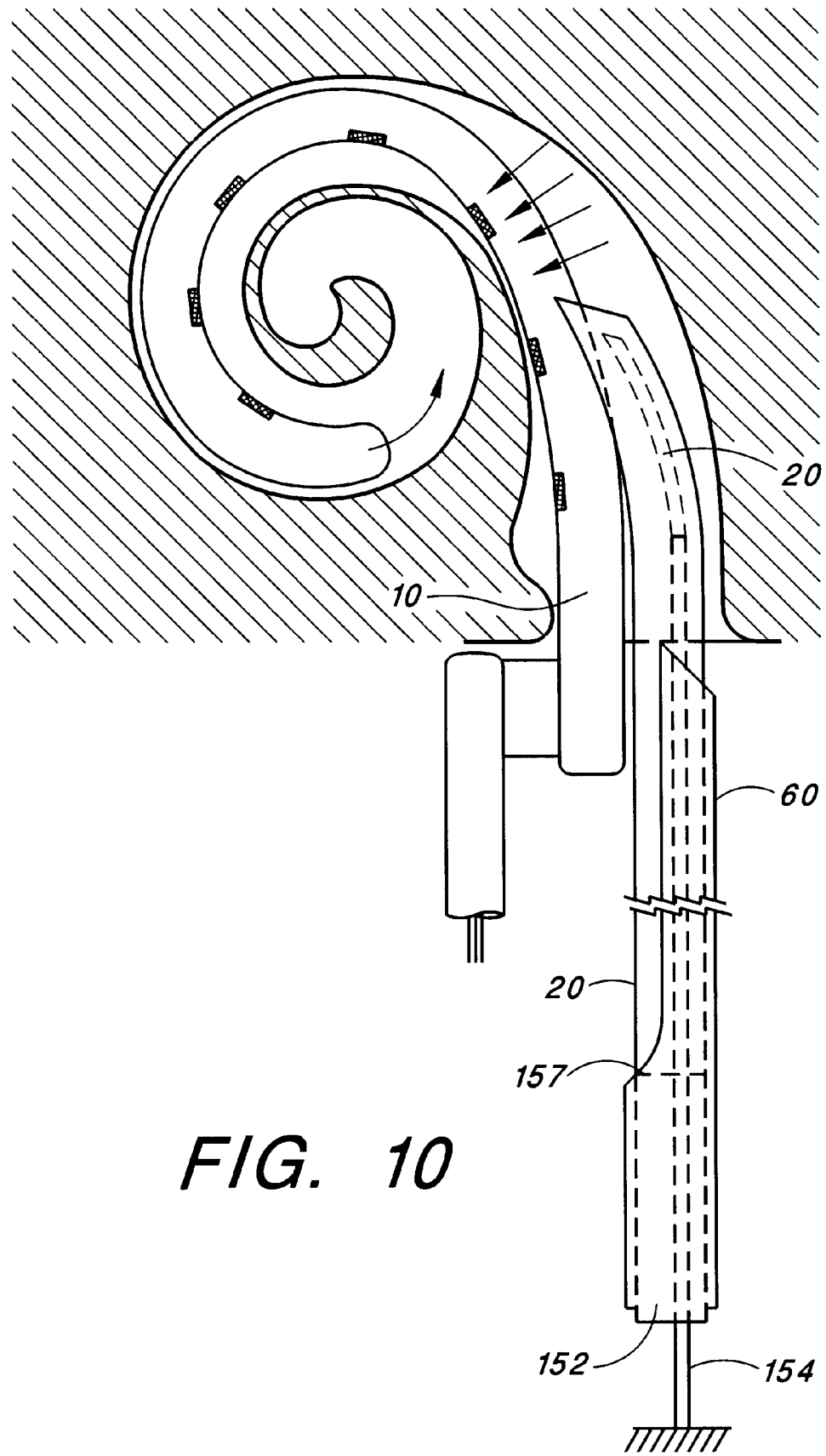
FIG. 10 illustrates use of the tool of the present invention during a positioner insertion mode.

Next, with reference to FIG. 10, the manner of using the insertion tool 150 of the present invention during a positioner insertion mode is illustrated. As seen in FIG. 10, the positioner 20 is inserted behind the electrode array, after the electrode array has been inserted into the cochlea. The positioner 20 is threaded onto the distal end of the stylet 154 by inserting the stylet into the hole or channel 27 of the positioner. The positioner lies within the open half cylinder portion 162 of the guiding tube 160 during this process. Note that the stylet 154 is locked in its positioner insertion mode position (see FIG. 7B). The pushing tube is then pushed towards the distal end, causing the distal tip 157 of the pushing tube 152 to engage a proximal end of the positioner 20, thereby pushing the positioner 20 deeper into the cochlea. As the positioner 20 is thus pushed deeper into the cochlea, the electrode array may also be pushed somewhat deeper into the cochlea.

It is thus seen that the present invention provides a positioner, and an insertion tool that makes insertion of the positioner 20 and/or electrode array into a human cochlea a safe and easy task to perform.

While the invention herein disclosed has been described by means of specific embodiments and applications thereof, numerous modifications and variations could be made thereto by those skilled in the art without departing from the scope of the invention set forth in the claims.

What is claimed is:

1. A method of positioning an implantable cochlear electrode array against a modiolar wall of a cochlea comprising:

inserting an electrode array into the cochlea;

inserting an elongate flexible positioner into the cochlea, with the electrode array being positioned between the modiolar wall and the positioner;

wherein the positioner positions the electrode array against the modiolar wall.

2. The method of claim 1 wherein the elongate flexible positioner has a curved distal end, a channeling groove along one side of the positioner, with the channeling groove residing on the same side of the positioner as the inside of the curve, and a lumen passing longitudinally therethrough, wherein the method further comprises:

inserting at least a portion of a stylet wire into the lumen; and using the stylet wire to guide insertion of the positioner into the cochlea.

3. The method of claim 2 wherein inserting the flexible positioner into the cochlea comprises inserting the flexible positioner into the cochlea with the channeling groove facing the modiolar wall, and with the electrode array being received within the channeling groove.

4. The method of claim 3 wherein inserting the elongate flexible positioner is facilitated by cutting a distal tip of the flexible positioner at a desired angle ($\alpha 1$).

5. The method of claim 1 wherein the positioner has a lumen passing longitudinally therethrough, and wherein inserting the positioner into the cochlea comprises inserting at least a portion of a stylet wire into the lumen to guide insertion of the positioner into the cochlea.

6. The method of claim 1 wherein the positioner has a channeling groove along one side of the positioner, and wherein inserting the positioner into the cochlea comprises inserting the positioner with the channeling groove facing the modiolar wall, and with the electrode array being received within the channeling groove.

7. A method of positioning an implantable cochlear electrode array against a modiolar wall of a human cochlea comprising:

forming an elongate flexible positioner;

inserting the cochlear electrode array into the cochlea;

inserting the flexible positioner into the cochlea, with the electrode array being positioned between the modiolar wall and the positioner;

wherein the positioner positions the electrode array adjacent the modiolar wall.

8. The method of claim 7 wherein the elongate flexible positioner is formed to have a desired size and shape, the desired shape including a curved distal end, a channeling groove along one side of the positioner, with the channeling groove residing on the same side of the positioner as the inside of the curve, and a lumen passing longitudinally therethrough, wherein the method further comprises removably inserting a stylet wire into the lumen of the positioner, whereby the stylet wire aids insertion of the positioner into the cochlea.

9. The method of claim 8 wherein inserting the flexible positioner into the cochlea comprises placing a distal end of the positioner and stylet wire inside of the cochlea, and while holding the stylet wire, sliding the positioner off of the stylet wire, thereby guiding the positioner deeper into the cochlea as the positioner is slid off of the stylet wire.

10. The method of claim 8 further including forming a tab at a proximal end of the positioner on the same side of the positioner as the channeling groove.

11. The method of claim 8 wherein forming the positioner to have a desired size and shape comprises forming the positioner to have a straight section, beginning at a proximal end.

12. The method of claim 11 wherein forming the positioner further includes forming the straight section to have a length of about 0.6 inches, and forming the curved distal end to have a radius of curvature of between about 0.117 and 0.197 inches.

13. The method of claim 7 wherein the positioner is formed to have a lumen passing longitudinally therethrough, and wherein inserting the positioner into the cochlea comprises inserting at least a portion of a stylet wire into the lumen to guide insertion of the positioner into the cochlea.

14. The method of claim 7 wherein the positioner is formed to have a channeling groove along one side of the positioner, and wherein inserting the positioner into the cochlea comprises inserting the positioner with the channeling groove facing the modiolar wall, and with the electrode array being received within the channeling groove.

15. A method of positioning an implantable cochlear electrode array against a modiolar wall of a human cochlea comprising:

forming an elongate flexible positioner;

inserting the flexible positioner into the cochlea;

inserting the electrode array into the cochlea, with the electrode array being positioned between the modiolar wall and the positioner;

wherein the positioner positions the electrode array adjacent the modiolar wall.

16. The method of claim 15 wherein the positioner is formed to have a lumen passing longitudinally therethrough, and wherein inserting the positioner into the cochlea comprises inserting at least a portion of a stylet wire into the lumen to guide insertion of the positioner into the cochlea.

17. The method of claim 16 wherein inserting the positioner into the cochlea further comprises placing a distal end of the positioner and stylet wire inside the cochlea, and while holding the stylet wire, sliding the positioner off the stylet wire, thereby guiding the positioner deeper into the cochlea as the positioner is slid off the stylet wire.

18. The method of claim 15 wherein the positioner is formed to have a channeling groove along one side of the positioner, and wherein inserting the positioner into the cochlea comprises inserting the positioner with the channeling groove facing the modiolar wall, and with the electrode array being received within the channeling groove.

19. The method of claim 15 further including forming a tab at a proximal end of the positioner, which tab aids insertion of the positioner into the cochlea.

* * * * *